United States Patent [19]

Negre

[11] Patent Number: 5,643,194

[45] Date of Patent: Jul. 1, 1997

[54] SUBCUTANEOUS VALVE AND DEVICE FOR EXTERNALLY SETTING IT

[75] Inventor: Philippe Negre, Bures-sur-Yvette, France

[73] Assignee: Sophysa, Orsay, France

[21] Appl. No.: 494,793

[22] Filed: Jun. 26, 1995

[30] Foreign Application Priority Data

Jun. 24, 1994 [FR] France ................................. 94 07790

[51] Int. Cl.$^6$ ........................................... A61M 5/00
[52] U.S. Cl. ........................ 604/8; 604/9; 137/385; 251/65
[58] Field of Search ................... 604/8, 9; 137/385; 251/65

[56] References Cited

U.S. PATENT DOCUMENTS

| | | | |
|---|---|---|---|
| 4,443,214 | 4/1984 | Marion | 604/9 |
| 4,540,400 | 9/1985 | Hooven | 604/9 |
| 4,551,128 | 11/1985 | Hakim et al. | |
| 4,595,390 | 6/1986 | Hakim et al. | 604/9 |
| 4,676,772 | 6/1987 | Hooven | |
| 4,779,614 | 10/1988 | Moise | 604/9 |
| 5,167,615 | 12/1992 | East et al. | 604/9 |

FOREIGN PATENT DOCUMENTS

| | | | |
|---|---|---|---|
| 0421558 | 4/1991 | European Pat. Off. | 604/9 |
| 4370482 | 12/1992 | Japan | 251/65 |
| 9108001 | 6/1991 | WIPO . | |

Primary Examiner—John G. Weiss
Assistant Examiner—Francis K. Cuddihy
Attorney, Agent, or Firm—Schweitzer Cornman Gross & Bondell LLP

[57] ABSTRACT

A subcutaneous vane for the external regulation of fluid flow, said valve including a body comprising a substantially cylindrical and flat internal chamber having a central axis; an inlet pipe and a drain pipe formed in the lateral wall of said chamber and adapted to be connected respectively to a catheter for supplying a fluid and to a catheter for draining a fluid from said chamber; a rotor mounted in said chamber to rotate about said central axis; a non-return valve formed at the inner end of the inlet pipe and having a moveable valve element and a valve seat, said moveable valve element closing said valve when the valve element is engaged in the valve seat; a curved leaf spring fixed to said rotor generally parallel to the lateral wall of the chamber and urging the valve element into the valve seat; two micromagnets mounted in spaced relation in the motor on opposite sides of said central axis; locking means for locking the rotor in predetermined selected positions; the micromagnets being mounted to move linearly in said rotor in a substantially radial direction to actuate said locking means; whereby said locking means cannot be altered by strong external unidirectional magnetic fields and whereby said locking means can be locked only by a specifically applied bidirectional magnetic field.

6 Claims, 3 Drawing Sheets

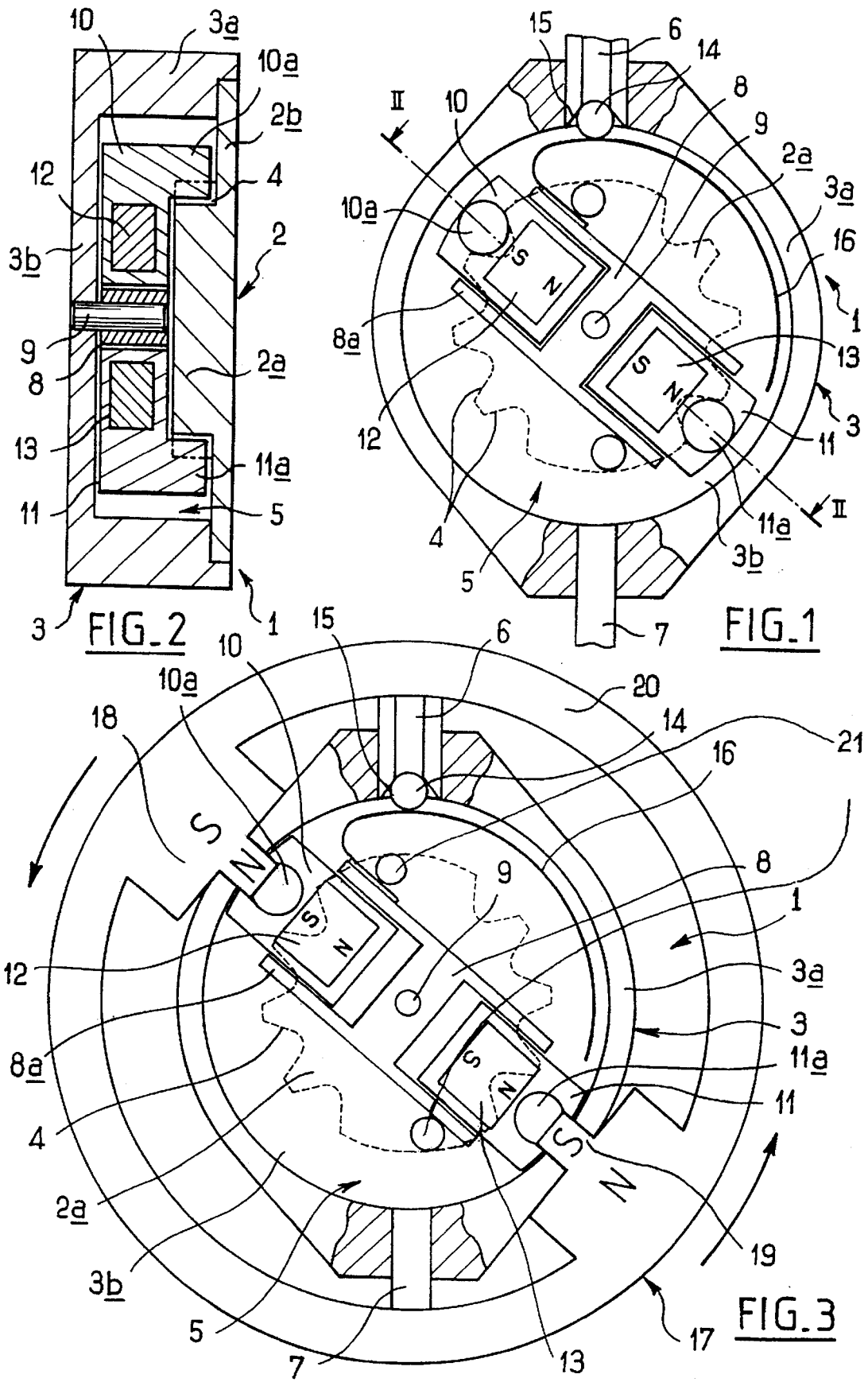

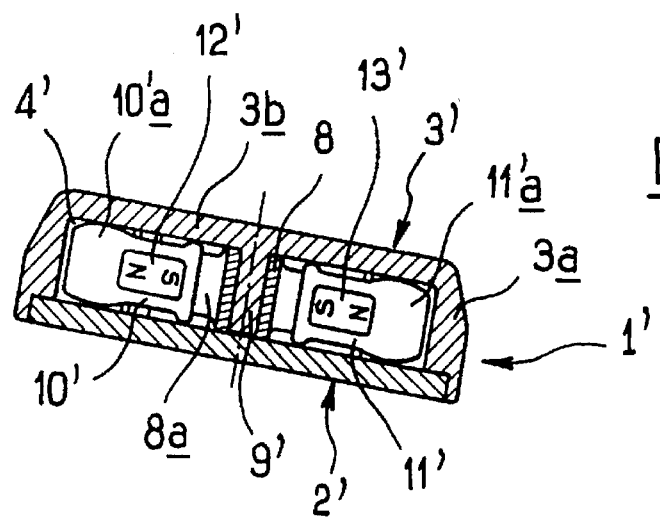
FIG. 5
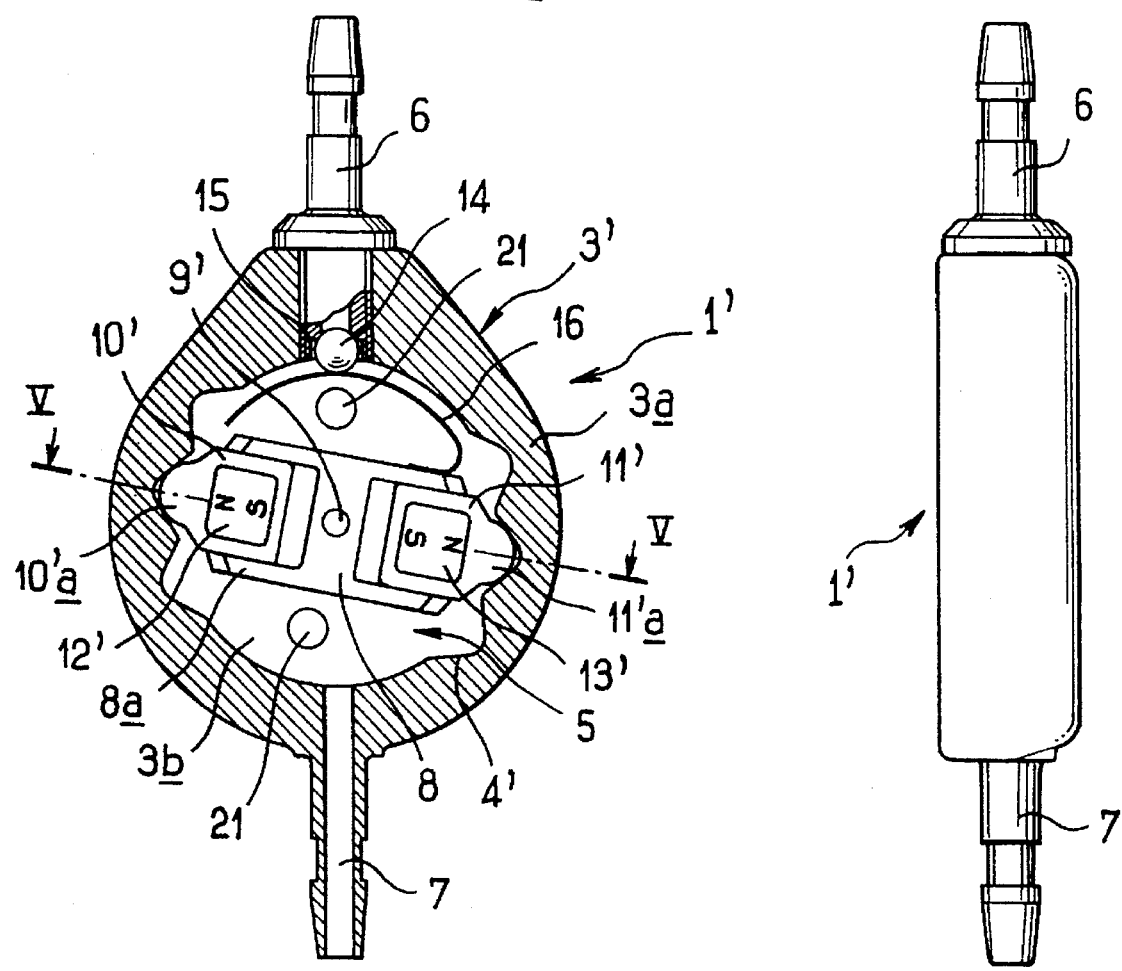
FIG. 4
FIG. 6

SUBCUTANEOUS VALVE AND DEVICE FOR EXTERNALLY SETTING IT

BACKGROUND OF THE INVENTION

The present invention relates to an improved subcutaneous valve intended for therapeutic applications and to a new and improved device for externally setting it which makes it possible to alter a passage or distribution of liquid into implanted systems or prostheses through the cutaneous tissues.

Among the therapeutic applications of the valve according to the invention, mention may be made of the treatment of hydrocephalus which consists in diverting the cerebrospinal fluid contained in the ventricles of the cranial cavity towards some other resorption site.

A known subcutaneous valve is described in French Patent No. 81 05389, corresponding to U.S. Pat. No. 4,443,214, of the Applicant Company.

Such prior art valve includes a body consisting of a substantially cylindrical and flat internal cheer, an inlet pipe and a drain pipe, formed in the lateral wall of the said chamber and capable of being connected respectively to a catheter for supplying a fluid and a catheter for draining a fluid away, a rotor able to turn in the said chamber about its central axis, a non-return valve, consisting of a ball and of a cone-shaped seat formed at the inner end of the inlet pipe, a semicircular leaf spring fixed to the said rotor, parallel to the lateral wall of the chamber and compressing the ball into its seat so as to regulate, and if appropriate block, the passage of fluid into the chamber via the inlet pipe, two micro-magnets mounted in the rotor and arranged on either side of the central axis of the chamber and means for locking the rotor in a determined position, the locking means including a lug projecting from one end of the rotor and cavities for accommodating the lugs, which cavities are formed in a circle in the lateral wall of the valve body, the said cavities having a shape desired to retain the said lugs.

Insofar as the prior art rotor includes micro-magnets, it is possible, by means of a magnet placed vertically in line with the valve, to drive the rotor in rotation through the wall of the valve and the cutaneous tissue covering it when the valve is implanted. It is thus possible to set the rotor into its various locked positions from a distance and from outside, and consequently to modify the operating throughput and pressure of the valve.

However, this type of valve with a magnetic rotor exhibits the drawback that its setting can be altered under the action of a strong external magnetic or electromagnetic field, such as the one encountered in nuclear magnetic resonance imaging.

This drawback is very uncomfortable for wearers of valves of the abovementioned type who have to have their valve reset after each examination employing techniques such as nuclear magnetic resonance imaging.

SUMMARY OF THE INVENTION

The object of the present invention is to supply a subcutaneous valve, the setting of which cannot be altered by an external magnetic field other than the one originating from a specific magnetic setting device.

The subject of the present invention is a sub-cutaneous valve intended for therapeutic applications allowing the external regulation of a distribution of fluid, the said valve including a body consisting of a substantially cylindrical and flat internal chamber, an inlet pipe and a drain pipe, formed in the lateral wall of the said chamber and capable of being connected respectively to a catheter for supplying a fluid and a catheter for draining a fluid away, a rotor able to turn in the said chamber about its central axis, a non-return valve, such as a ball, formed at the inner end of the inlet pipe, a curved leaf spring, preferably a semi-circular one, fixed to the said rotor, parallel to the lateral wall of the chamber and compressing the valve element into its seat so as to regulate, and if appropriate block, the passage of fluid into the chamber via the inlet pipe, two micro-magnets mounted in the rotor and arranged on either side of the central axis of the chamber and means for locking the rotor in a determined position, the valve being characterized in that the micro-magnets can move linearly in the said rotor in a substantially radial direction thereof, so as to actuate the said locking means.

The rotor advantageously consists of a bar in the shape of an H, the lateral branches of which serve as guide means for the moving micro-magnets.

The locking means preferably include a lug projecting from moving parts each one housing a micromagnet, and cavities for accommodating the lugs formed in a circle in the chamber, the said cavities having a shape which is designed to retain the said lugs.

In a first embodiment of the valve according to the present invention, the moving micro-magnets are arranged so as to attract each other, their opposing faces being of opposite polarities, and the cavities are formed at the periphery of a central part of the upper wall or lower wall of the valve body, the lugs projecting from the respective moving parts perpendicularly to the said upper wall or lower wall.

The upper wall or lower wall of the valve body advantageously consists of a removable cover which includes the said central part.

In a second embodiment of the valve according to the present invention, the moving micro-magnets are of like polarity and the said cavities are formed on the periphery of the lateral wall of the chamber, the studs projecting radially from the respective moving parts towards the said lateral wall.

Another subject of the present invention is a device for externally setting the valve according to the present invention.

According to a first embodiment, the external setting device according to the present invention consists of two magnets, the opposing faces of which are of opposite polarities to and which have a greater magnetic mass than the moving micro-magnets, the said magnets being mounted on a common support, preferably an annular or horseshoe shaped one, and spaced apart by a distance substantially equal to or greater than the distance separating the outer poles of the two moving micromagnets when the latter are actuating the locking means.

According to a second embodiment, the external setting device according to the present invention consists of a circular succession of magnetized poles mounted on a support, preferably an annular support, the poles of like polarity being arranged diametrally in twos and spaced apart by a distance substantially equal to or greater than that separating the outermost poles of the two moving micro-magnets when the latter are actuating the locking means.

According to a third embodiment, the external setting device according to the present invention includes a support, preferably an annular support, and electromagnetic means mounted in a circle on the said support, and arranged radially in the direction of the cavities for accommodating the lugs, the said electromagnetic means being capable of sending sequences of coded electromagnetic pulses corresponding to the various positions of locking of the rotor in the chamber.

In order to make the subject matter of the present invention easy to understand, there will be described hereinbelow, purely by way of illustrative non-limiting example, several embodiments thereof which are represented in the appended drawing, in which:

DESCRIPTION OF THE DRAWINGS

FIG. 1 is a partially sectioned plan view of the valve according to a first embodiment of the invention, FIG. 2 is a section on II—II of the valve of FIG. 1, FIG. 3 is a plan view of a first embodiment of the external setting device according to the present invention, placed vertically in line with the valve of FIG. 1, FIG. 4 is partially sectioned plan view of the valve according to a second embodiment of the invention, FIG. 5 is a section on V—V of the valve of FIG. 4, FIG. 6 is a lateral view of the valve of FIG. 4.

DETAILED DESCRIPTION OF THE INVENTION

Figure 7:
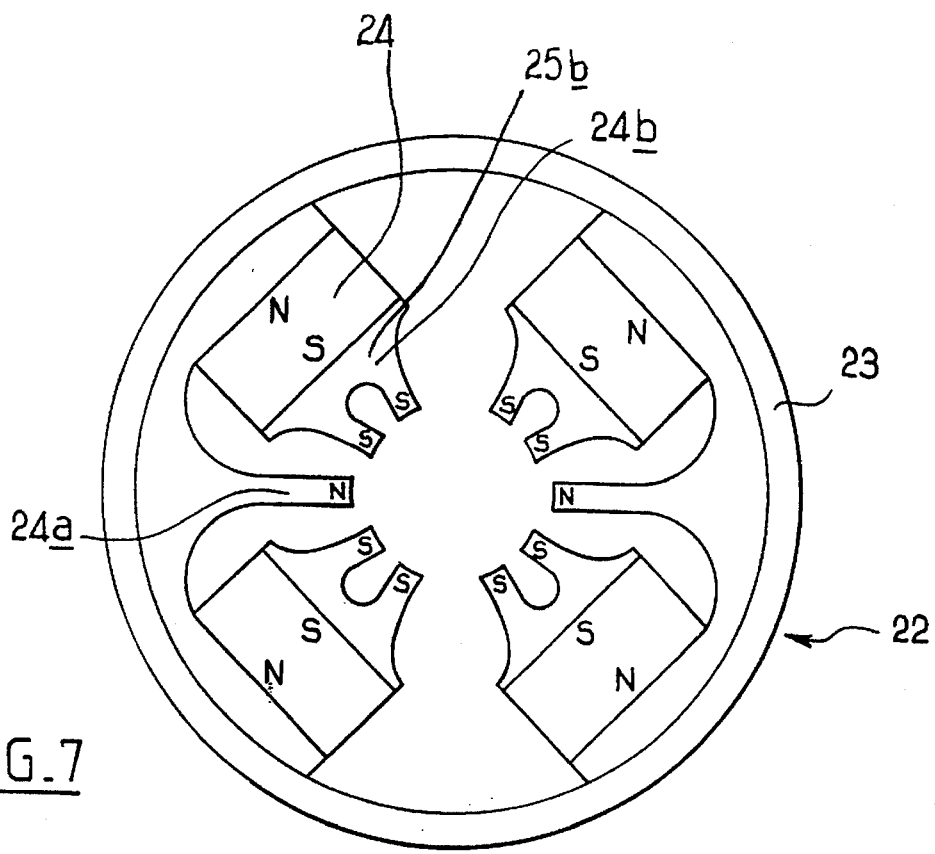
FIG. 7 is a plan view of a second embodiment of the external setting device according to the present invention.

FIG. 1 represents a plan view of a valve body 1, without its upper cover 2, for greater clarity.

The valve body 1 consists of an upper cover 2 and of a casing 3.

The upper cover 2 represented in section in FIG. 2, includes a substantially cylindrical central part 2a separated by a shoulder from a flat part 2b in the form of a flange.

Cavities 4, represented in broken line in FIGS. 1 and 3, are formed at the periphery of the central part 2a.

The peripheral part of the flange 2b rests in an annular recess formed in the upper end of the lateral wall 3a of the casing 3.

The valve body 1 includes a cylindrical and flat internal chamber 5 formed between the lower wall 3b, the lateral wall 3a of the casing 3 and upper cover 2.

An inlet pipe 6 and a drain pipe 7 are formed in the lateral wall 3a of the casing 3, the inner ends of the said pipes 6 and 7 being arranged diametrally in the chamber 5.

The inlet pipe 6 and the drain pipe 7 are capable of being connected respectively to a catheter for supplying fluid and to a catheter for draining fluid away, these catheters not being represented in the drawing.

A rotor 8 consisting of an H-shaped bar is mounted so that it can rotate in the chamber 5 about its central axis 9. Stop elements 21 projecting from the lower wall 3b of the casing 3 are provided, in order to limit the rotational displacement of the rotor 8.

The rotor 8 may advantageously be made of plastic.

The rotor 8 includes lateral branches 8a which serve as guide means, on either side of the central axis 9, for moving parts 10 and 11 each housing a micro-magnet 12 and 13, the opposing faces of the micro-magnets being of opposite polarity (N and S).

The moving parts 10 and 11 can move linearly inside the rotor 8 in a substantially radial direction thereof so as to actuate the locking means.

The locking means consist of cylindrical lugs 10a and 11a projecting respectively from the moving parts 10 and 11, and of the circular succession of cavities 4 able to accommodate the said lugs (10a and 11a).

The valve body 1 includes a non-return valve consisting of a ball 14 and of a cone-shaped seat 15 arranged at the inner end of the inlet pipe 6.

A semi-circular leaf spring 16 is fixed to one lateral branch 8a of the rotor 8, is parallel to the lateral wall 3a of the chamber 5 and compresses the ball 14 into its seat 15 so as to regulate, and if appropriate block, the passage of fluid into the chamber 5 via the inlet pipe 6.

FIG. 3 represents an external setting device 17 which is particularly suited to the first embodiment of the valve body 1.

The external setting device 17 consists of two magnets 18 and 19, for example made of samarium-cobalt, the opposing faces of which are of opposite polarities to (N and S) and of greater magnetic mass than the moving micro-magnets 12 and 13.

The magnets 18 and 19 are mounted on a common annular support 20, for example made of soft iron, diametrally opposed and spaced apart by a distance substantially equal to or greater than the distance separating the outer poles of the two moving micro-magnets 12 and 13 when the lugs 10a and 11a are engaged in the cavities 4.

FIGS. 4 to 6 represent a second embodiment of the valve body 1' according to the present invention.

The valve-body 1' consists of a casing 3' and of a disc-shape upper cover 2'.

The casing 3' includes, projecting from the lower wall 3b, a central part 9' forming the central axis of the chamber 5.

Two parts 10' and 11' are mounted so that they can move between the lateral branches 8a of the rotor 8, on either side of the central axis 9'.

The moving parts 10' and 11' respectively include a lug 10'a and 11'a which projects radially from the respective moving part towards the lateral wall 3a of the casing 3' and each one accommodates a micro-magnet 12' and 13', the micro-magnets being arranged so as to repel one another, being of like polarity (S or N).

The locking means consist of the said lugs 10'a and 11'a which are capable of engaging in the cavity 4' made at the internal periphery of the lateral wall 3a of the chamber 5.

The chamber 5 further includes stop elements 21 projecting from the lower wall 3b of the casing 3' in order to limit the rotational displacement of the rotor 8.

FIG. 7 represents an external setting device 22 which is particularly suited to the second embodiment of the valve according to the present invention.

The external setting device 22 consists of an annular support 23 and of magnets 24, the opposing faces of which are of like polarity (N or S), the field lines of these magnets are channelled by pieces of soft iron 25a, 25b designed so as to produce a magnetic ring formed of a circular succession of magnetized poles pointing radially towards the centre of the support 23. These magnetized poles are furthermore arranged diametrically in twos so that two poles situated on one and the same diameter are of identical polarity and are spaced apart by a distance substantially equal to or greater than that separating the outer poles of the two moving micromagnets 12' and 13' when the lugs 10'a and 11'a are engaged in the cavities 4'.

It can be seen in FIG. 7 that two N poles are symmetrically surrounded on all sides our S poles.

Figure 8:
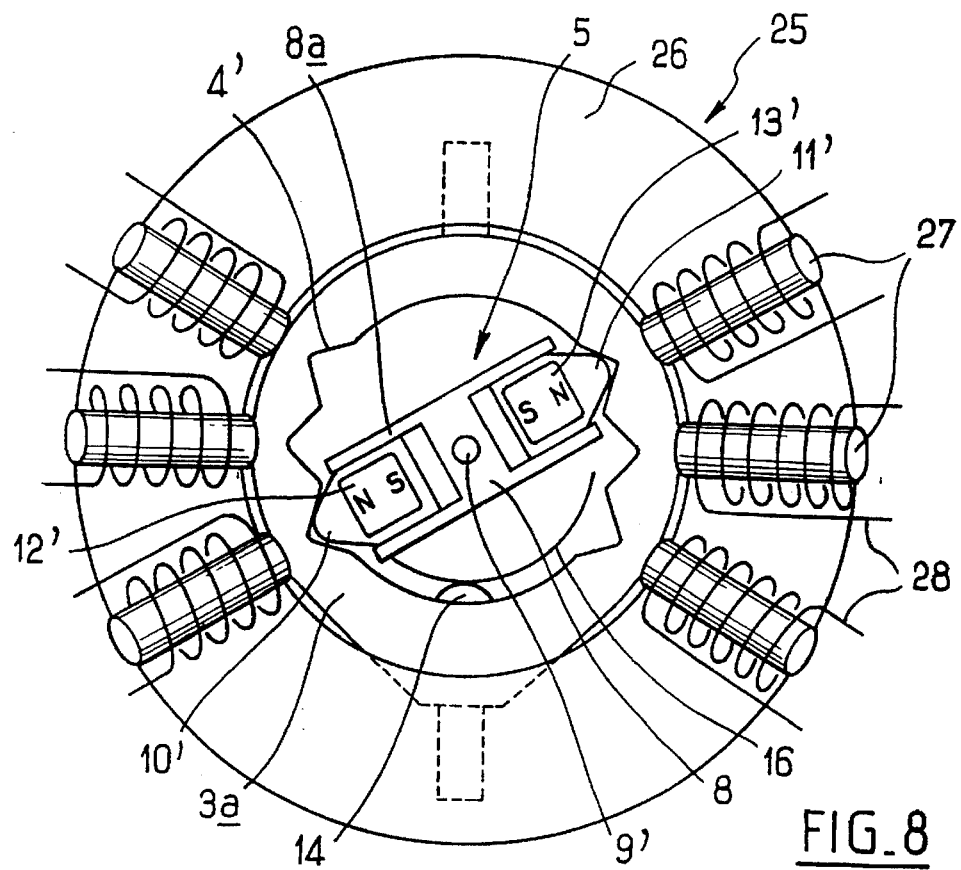
FIG. 8 is a plan view of a third embodiment of the external setting device according to the present invention, placed vertically in line with the valve of FIG. 4.

FIG. 8 represents a third embodiment of an external setting device 25 according to the present invention.

The external setting device 25 includes an annular support 26 and electromagnetic means mounted in a circle on the said support 26.

The electromagnetic means consist of magnetic rods 27 around which coils 28 are wound.

The bars 27 are arranged radially in the direction of the accommodating cavities 4'.

The operation of these external setting devices will now be described.

FIG. 1 represents the valve body 1 in its locked position, the lugs 10a and 11a being engaged in the cavities 4.

The micro-magnets lock the valve as a result of magnetic attraction brought about by the opposite polarities of the micro-magnets 12 and 13.

In general, the position of the rotor in the subcutaneous valve is determined by means of a compass applied vertically in line with the valve. This position may equally well be identified by means of a system employing digital Hall-effect probes associated with light-emitting diodes, or using any other electromagnetic means.

FIG. 3 represents the valve body 1 in its unlocked position, the studs 10a and 11a both being disengaged from the cavities 4.

In order to unlock the valve, the external setting device 17 illustrated in FIG. 3 is placed vertically in line with the valve body 1 so that the magnets 18 to 19, the opposing faces of which have opposite polarities (N and S) are positioned symmetrically with respect to the central axis 9 of the chamber 5 and on either side of the micro-magnets 12 and Bearing in mind the difference in magnetic mass which exists between the magnets of the external setting device and the micro-magnets of the valve, the simple fact of bringing the N and S poles of the jetting device close to the opposite S and N poles of the micro-magnets, subjects the two outer poles of the micro-magnets to a peripheral attraction which is greater than the central mutual attraction between the two inner poles. This results in the two micro-magnets together with their moving parts separating symmetrically and simultaneously towards the periphery of the chamber, which unlocks the rotor and renders it free to rotate. With the rotor thus unlocked, it is possible to alter its position and consequently to alter the operating pressure and throughput of the valve, by pivoting the setting device about the central axis of the chamber of the valve, which simultaneously drives the rotor along. In order to lock the rotor in a new determined position, all that is required is to withdraw the setting device, moving it away vertically with respect to the plane of the valve. As the two micro-magnets are no longer subjected to external peripheral attraction, they approach each other again under the effect of their mutual attraction, thus locking the moving parts.

This type of valve with moving micro-magnets cannot lose its setting in the presence of a strong external magnetic or electromagnetic field, because the two moving micro-magnets cannot simultaneously disengage from their cavity in the presence of a unidirectional magnetic field.

Insofar as the two moving micro-magnets 12 and 13 are arranged on either side of the central axis of the valve, when one of the micro-magnets is attracted towards the periphery of the chamber, the other is repelled into a locking cavity.

It is necessary to apply a specific setting device like the one illustrated in FIG. 3 in order to unlock the valve, that is to say in order to separate the micro-magnets symmetrically.

Of course, the strength of the magnet has to be greater than that of the micro-magnets so as to overcome the attraction force which exists between the micromagnets.

FIG. 4 represents the valve body 1' in a locked position, the studs 10'a and 11'a being engaged in the cavities 4', owing to the repulsion generated by the arrangement of the micro-magnets 12' and 13', the opposing faces of which are of identical polarity (S).

FIG. 7 represents an external setting device 22 capable of unlocking the valve 1' illustrated in FIG. 4.

Here, unlocking is achieved by placing the external setting device 22 vertically in line with the valve body 1' so that the two magnetized poles 25a of identical polarity (N) are positioned symmetrically with respect to the axis 9' of the chamber 5 on either side of the micro-magnets 12' and 13'.

The micro-magnets 12' and 13' then disengage from the cavities 4' following the repulsion generated by the identical polarity which exists between the magnetized poles 25a and the micro-magnets 12' and 13'.

The micro-magnets 12' and 13' are therefore in unstable equilibrium and tend to move, by attraction, towards the closest magnetized pole 25b of opposite polarity (S), thus locking the rotor in a new position.

By rotating the external setting device 22 about the central axis 9', the rotor 8 is thus made to move from cavity to cavity.

Just like the type of valve locked by magnetic attraction described previously with reference to FIG. 1, this type of valve locked by magnetic repulsion is also unable to lose its setting in the presence of a strong external magnetic or electromagnetic field, because the two moving micro-magnets cannot simultaneously disengage from their cavity in the presence of a unidirectional magnetic field. Insofar as the two moving micro-magnets 12' and 13' are arranged on either side of the central axis of the valve, when one of the micro-magnets is attracted towards the centre of the valve, the other is pushed back into a locking cavity. It is necessary to apply a specific setting device such as those illustrated in FIG. 7 and FIG. 8 in order to unlock the valve, that is to say in order to move the micro-magnets together symmetrically. Of course, the magnetic or electromagnetic field created by the setting device must be stronger than that which exists between the two micro-magnets so as to over come the repulsive force which keeps them apart.

FIG. 8 represents an electromagnetic external setting device 25 superimposed on the second embodiment of the valve according to the invention, namely the valve body 1'.

This electromagnetic external setting device 25 is not, however, limited to the valve body 1' but may quite well be applied to the first embodiment of the valve, namely the valve body 1.

This electromagnetic external setting device 25 can be programmed in advance and it can send sequences of coded electromagnetic pulses corresponding to the various locked positions of the rotor 8 in the chamber 5 via electromagnetic means consisting of the magnetic bars 27 and the coils 28.

Although the invention has been described in conjunction with specific embodiments, it is quite clear that it is in no way limited thereto and that many variations and modifications can be made thereto without thereby departing from its scope or from its spirit.

Likewise, the valve according to the invention can be used in applications other than the treatment of hydrocephalus, and especially for example for producing artificial urinary sphincters or systems for distributing drugs, such as morphine, insulin, or anti-cancer drugs.

We claim:

1. A subcutaneous valve structure for the external regulation of fluid flow,
   a) said subcutaneous valve structure, including a body with a periphery and comprising a substantially cylindrical and flat internal chamber having a central axis and a lateral wall;
   b) an inlet pipe with an inner end and a drain pipe formed in the lateral wall of said chamber and adapted to be connected respectively to a catheter for supplying a fluid and to a catheter for draining a fluid from said chamber;
   c) a non-return valve formed at the inner end of the inlet pipe and comprising a moveable valve element and a valve seat, said moveable valve element closing said valve when the valve element is engaged in the valve seat;
   d) a rotor mounted in said chamber to rotate about said central axis;
   e) a curved leaf spring fixed to said rotor generally parallel to the lateral wall of the chamber and urging the valve element into the valve seat;
   f) locking means for locking the rotor in predetermined selected positions;
   g) two micromagnets of predetermined polarities mounted in spaced relation in the rotor on opposite sides of said central axis;
   h) the micromagnets being mounted to move linearly in said rotor in a substantially radial direction to actuate said locking means;
   i) whereby said locking means cannot be altered by strong external unidirectional magnetic fields and whereby said locking means can be locked only by an applied bidirectional magnetic field of predetermined strength.

2. A subcutaneous valve according to claim 1, wherein a rotor comprises
   a) a bar having a generally H shape with lateral branches;
   b) the lateral branches of said H-shaped rotor serving as guide means for the two moveable micromagnets which are mounted in said rotor adjacent said guide means.

3. A subcutaneous valve according to claim 2, wherein
   a) said locking means includes lugs projecting from moveable elements and a series of cavities; and
   b) said lugs are adapted to engage selected ones of said cavities for locking said rotor in a predetermined selected position, each selected position corresponding to a different valve setting.

4. A subcutaneous valve according to claim 3, wherein
   a) the polarities of the micromagnets are oppositely arranged to attract each other; and
   b) wherein the cavities are formed at the periphery of the chamber;
   c) the lugs projecting from said moveable elements being arrayed perpendicularly to the wall.

5. A subcutaneous valve according to claim 4 which includes a removable cover.

6. A subcutaneous valve according to claim 3, wherein
   a) the polarities of the micromagnets are arranged to be alike to repel one another;
   b) said micromagnets having opposing faces of the same polarity;
   c) said cavities are formed at the periphery of the valve body chamber;
   d) the lugs projecting radially from the respective moveable elements towards said lateral wall.

* * * * *